US009017362B2

(12) United States Patent
Hardert et al.

(10) Patent No.: US 9,017,362 B2
(45) Date of Patent: Apr. 28, 2015

(54) OCCLUDING DEVICE

(75) Inventors: Michael W. Hardert, Bloomington, IN (US); Sarah E. Waite, Cory, IN (US); Arman H. Valaie, Bloomington, IN (US); Kevin L. Delaney, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 1388 days.

(21) Appl. No.: 11/762,570

(22) Filed: Jun. 13, 2007

(65) Prior Publication Data

US 2008/0312679 A1 Dec. 18, 2008

(51) Int. Cl.
*A61M 29/00* (2006.01)
*A61B 17/12* (2006.01)
*A61B 17/00* (2006.01)

(52) U.S. Cl.
CPC ..... *A61B 17/12022* (2013.01); *A61B 17/12136* (2013.01); *A61B 17/12159* (2013.01); *A61B 17/12163* (2013.01); *A61B 17/12168* (2013.01); *A61B 17/12181* (2013.01); *A61B 2017/00867* (2013.01); *A61B 2017/00898* (2013.01); *A61B 2017/12054* (2013.01)

(58) Field of Classification Search
USPC .......................... 606/108, 194, 200; 128/831
See application file for complete search history.

(56) References Cited

U.S. PATENT DOCUMENTS

| 5,499,995 | A | 3/1996 | Teirstein |
| 5,527,338 | A | 6/1996 | Purdy |
| 5,656,036 | A | 8/1997 | Palmaz |
| 5,916,235 | A * | 6/1999 | Guglielmi ..................... 606/200 |
| 6,375,671 | B1 | 4/2002 | Kobayashi et al. |
| 6,428,558 | B1 | 8/2002 | Jones et al. |
| 6,432,116 | B1 | 8/2002 | Callister et al. |
| 6,517,559 | B1 * | 2/2003 | O'Connell ..................... 606/158 |
| 6,585,756 | B1 | 7/2003 | Strecker |
| 6,994,092 | B2 | 2/2006 | Van der Burg et al. |
| 6,994,717 | B2 | 2/2006 | Konya et al. |
| 7,083,632 | B2 | 8/2006 | Avellanet et al. |
| 7,122,043 | B2 | 10/2006 | Greenhalgh et al. |
| 2003/0028213 | A1 | 2/2003 | Thill et al. |
| 2003/0139819 | A1 | 7/2003 | Beer et al. |
| 2003/0229366 | A1 | 12/2003 | Reggie et al. |
| 2005/0045183 | A1 * | 3/2005 | Callister et al. ............... 128/831 |
| 2005/0070993 | A1 * | 3/2005 | Boekstegers et al. ........ 623/1.25 |
| 2005/0096735 | A1 * | 5/2005 | Hojeibane et al. ........... 623/1.24 |
| 2005/0192616 | A1 * | 9/2005 | Callister et al. .............. 606/193 |
| 2006/0058833 | A1 | 3/2006 | VanCamp et al. |
| 2006/0116712 | A1 * | 6/2006 | Sepetka et al. ................ 606/200 |
| 2006/0217762 | A1 | 9/2006 | Maahs et al. |
| 2006/0235464 | A1 * | 10/2006 | Avellanet et al. ............. 606/200 |
| 2007/0227544 | A1 * | 10/2007 | Swann et al. ................. 128/831 |

* cited by examiner

*Primary Examiner* — Katherine Dowe
(74) *Attorney, Agent, or Firm* — Brinks Gilson & Lione

(57) ABSTRACT

An occluding device for occlusion within a body vessel is disclosed. The device comprises an expandable frame having an occluding portion disposed within a closure area of the frame. An anchoring component is attached to the frame to engage the body vessel. A coupling is attached to the frame for repositioning the device.

12 Claims, 3 Drawing Sheets

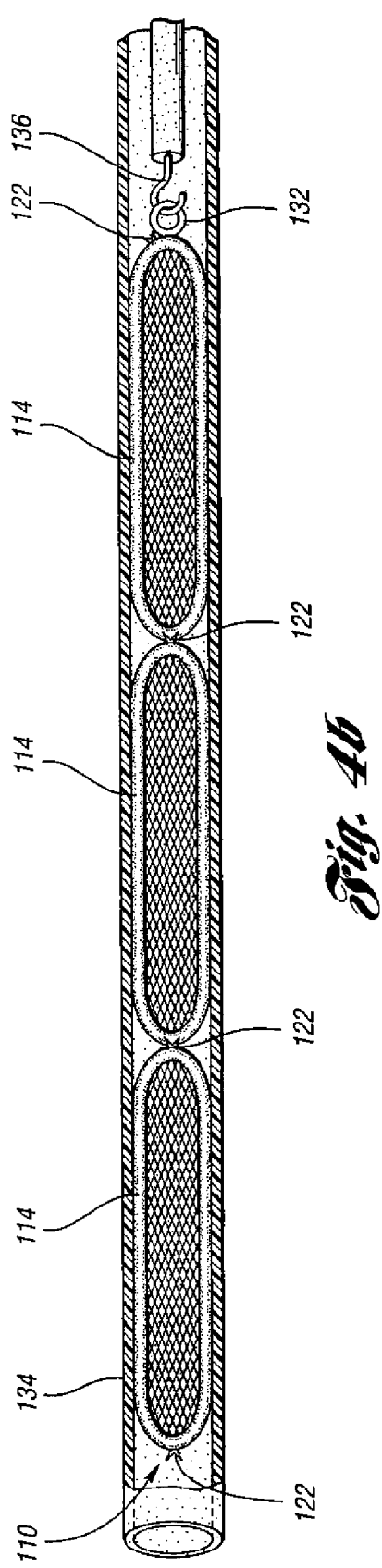
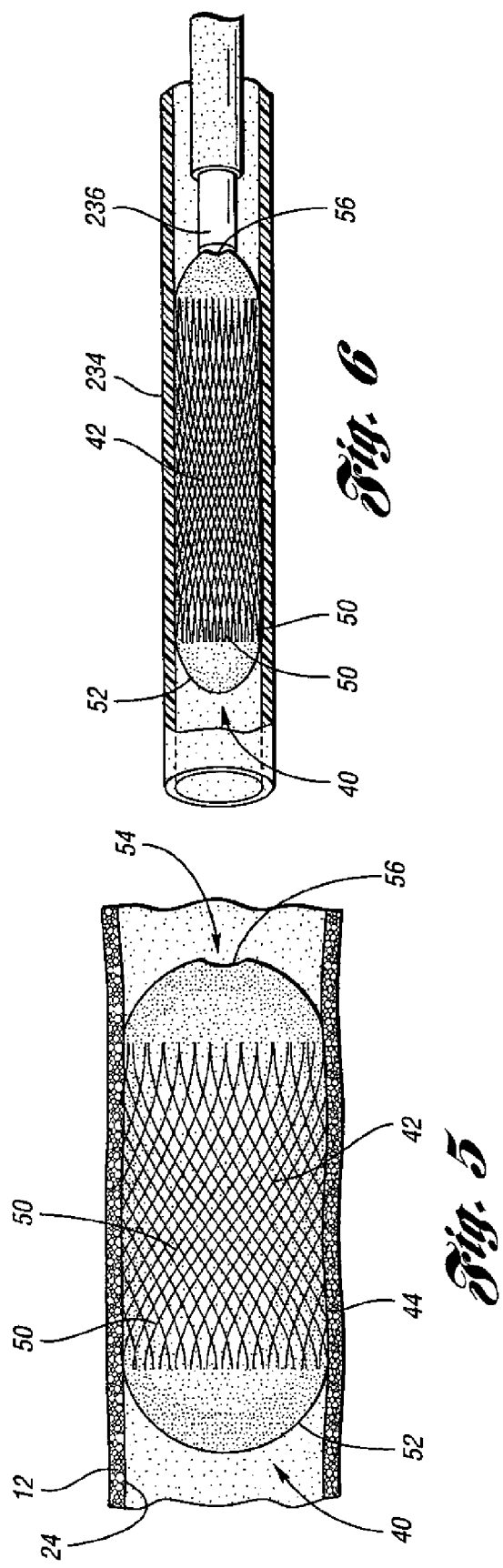

OCCLUDING DEVICE

BACKGROUND OF THE INVENTION

1. Field of the Invention

The present invention generally relates to medical devices. More particularly, the invention relates to occluding devices for occlusion within body vessels.

2. Description of Related Art

A number of different devices may be used to occlude a body vessel, such as a blood vessel. Some occluding devices are temporary and others are permanent or semi-permanent. An example of permanent occlusion devices are embolization coils comprising occluding material, which may be inserted into a vein or artery percutaneously, in order to occlude the body vessel. Embolization coils are permanent and promote blood clots or tissue growth over a period of time, thereby occluding the body vessel. Generally, a plurality of coils, for example, five to ten coils, is required to occlude the body vessel. Such coils must be carefully positioned, in order to avoid migration, and there is generally no way to reposition the coils.

In view of the above, there exists a need for a permanent or semi-permanent occlusion device that is resistant to migration and that may be implemented to effectuate occlusion in a simple manner.

BRIEF SUMMARY OF THE INVENTION

The present invention provides an occlusion device, which may be permanent or semi-permanent for occluding within a body vessel. The device is resistant to migration and simple to implement. The various embodiments of the present invention include a single occluding device to be delivered into the body vessel to occlude the body vessel.

In satisfying the above needs as well as overcoming the enumerated drawbacks and other limitations of the related art, the present invention provides an occluding device for occlusion within a body vessel. In one embodiment, the device includes at least one frame which has a closure area defined therein. The frame has an expanded state and a collapsed state. An occluding portion is disposed within the closure area of the frame. At least one anchoring component is attached to the outer edge of the frame. The anchoring component is configured to engage the occluding device within a body vessel for reducing migration of the device. A coupling is attached to the outer edge of the frame for positioning or repositioning the occluding device.

In another aspect, an occluding device for occlusion within a body vessel is provided, which includes an expandable body and an expandable balloon. The expandable body has an outer perimeter that is configured to engage the inner diameter of the body vessel when the expandable body is in an open state. The expandable body is configured to self-expand in the open state, and the expandable body is further configured to collapse in a collapsed state upon exertion of a force to the outer perimeter of the expandable body. The expandable balloon is disposed about the expandable body to expand as the expandable body self-expands in the open state. The expandable balloon has an open end that has an opening to receive fluid in the balloon in the open state for occlusion within the body vessel.

In another aspect, an occluding device for occlusion within a body vessel is provided, which includes a compressible foam body for occlusion within the body vessel. A plurality of struts is disposed about the foam body. The struts have first ends attached together at a proximal portion, and each strut extends from the first end to a second portion. The second portions of the struts are disposed about the foam body. The struts are configured to move between an expanded state for engaging the body vessel and a collapsed state for a device retrieval or delivery. The second portions of the struts have at least one anchoring component configured to engage the body vessel when the struts are in the expanded state. A positioning coupling extends from the proximal portion for delivery or repositioning of the device.

Further objects, features and advantages of this invention will become readily apparent to persons skilled in the art after a review of the following description, with reference to the drawings and claims that are appended to and form a part of this specification.

BRIEF DESCRIPTION OF THE DRAWINGS

FIG. 4b is a side view of the occluding device of FIG. 4a in a collapsed state;

FIG. 5 is an environmental view of an occluding device in accordance with another embodiment of the present invention;

FIG. 6 is a side view of the occluding device of FIG. 5 in a collapsed state;

DETAILED DESCRIPTION OF THE INVENTION

The present invention generally provides an occluding device for occlusion of a body vessel. The device is preferably delivered percutaneously. The various embodiments of the present invention are resistant to migration and include merely a single occluding device to be delivered into a body vessel to occlude the body vessel. Embodiments of the present invention generally provide an occlusion device intended for permanent occlusion within a body vessel; however, it is contemplated that the invention could also be used for temporary occlusion.

Figure 1:
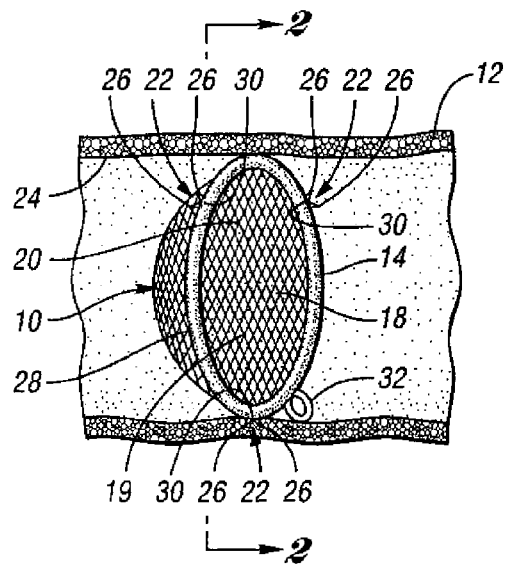
FIG. 1 is an environmental view of an occluding device in accordance with one embodiment of the present invention.

Referring now to FIG. 1, an occluding device 10 embodying the principals of the present invention is illustrated therein. The occluding device 10 is disposed within a body vessel 12, such as a vein, artery, or any other body vessel having a diameter preferably in the range of about four millimeters to about twenty millimeters. It is also contemplated that body vessels having even smaller diameters could also be used with the occluding device 10.

The occluding device 10 preferably has an annular frame 14. In the alternative, it is contemplated that the frame could have shapes other than an annulus, such an oval, for example, without falling beyond the scope or spirit of the present invention.

The annular frame 14 has a closure area 18, and an occluding portion 19 disposed within the closure area 18. The occluding portion 19 preferably comprises a membrane 20 having occluding material. The membrane 20 is preferably relatively thin and flexible, and comprises occluding material such as small intestinal submucosa (SIS), synthetic polyester, such as DACRON™, or urethane. The flexible material preferably is either stretchable or oversized to accommodate the collapsed state of the annular frame 14, as will be discussed in further detail below.

As known, SIS is a resorbable, acellular, naturally occurring tissue matrix composed of extracellular matrix (ECM) proteins and various growth factors. SIS is derived from the porcine jejunum and functions as a remodeling bioscaffold for tissue repair. SIS has characteristics of an ideal tissue engineered biomaterial and can act as a bioscaffold for remodeling of many body tissues including skin, body wall, musculoskeletal structure, urinary bladder, and also supports new blood vessel growth. SIS may be used to induce site-specific remodeling of both organs and tissues depending on the site of implantation. In practice, host cells are stimulated to proliferate and differentiate into site-specific connective tissue structures, which have been shown to completely replace the SIS material in time.

In this embodiment, SIS is used to occlude the body vessel 12, adhere to the walls 24 of the body vessel 12 in which the device 10 is deployed, and promote body tissue growth within the body vessel 12. SIS has a natural adherence or wetability to body fluids and connective cells comprising the connective tissue of the walls of a body vessel 12. Since the device 10 is intended to permanently occlude the body vessel 12, the device 10 is positioned such that the host cells of the wall 24 will adhere to the SIS and subsequently differentiate, growing into the SIS and eventually occluding the body vessel 12 with the tissue of the walls 24 to which the device 10 was originally adhered. This feature enhances permanent occlusion of the body vessel 12.

In another particular embodiment, the SIS may be used to temporarily adhere the device 10 to the walls 24 of the body vessel 12. If the device 10 is only deployed within the body vessel 12 temporarily, host cells of the walls 24 may adhere to the device 10, but will not differentiate, allowing for later retrieval of the device 10 from the body vessel 12.

In another embodiment, the membrane 20 may comprise synthetic fibers, such as DACRON™, to occlude in the closure area 18. The fibers could be woven into a textile membrane or could be connected to a membrane having a different material. The membrane 20 is preferably oversized to accommodate the collapsed state of the annular frame 14, which will be described in further detail below. The fibers and the membrane 20 could have other configurations without falling beyond the scope or spirit of the present invention. For example, a urethane membrane 20 could be used to occlude within the closure area 18. The urethane membrane 20 could be comprised of a urethane or polyurethane material and extend across the closure area 18. The urethane membrane 20 is preferably stretchable to accommodate the collapsed state of the annular frame 14, as will be described in further detail below.

Furthermore, the occluding device 10 has anchoring components 22 for engaging the inside wall 24 of the body vessel 12 to reduce migration of the occluding device 10. The anchoring components 22 are disposed on the outer edge 28 of the annular frame 14. In this embodiment, the occluding device 10 has three anchoring components 22, in order to reduce migration of the device 10; however, it is contemplated that the device 10 could have any number of anchoring components 22 without falling beyond the spirit and scope of the present invention.

In this embodiment, the anchoring components 22 each comprise two prongs 26 extending from a common hub or point 30. In this way, the anchoring components 22 resemble barbs and retain the tissue wall 24 of the body vessel 12. The anchoring components 22 could alternatively be of any other configuration, such as, for example, single prongs extending from the outer edge 28 of the annular frame 14 without falling beyond the scope or spirit of the present invention.

Figure 2:
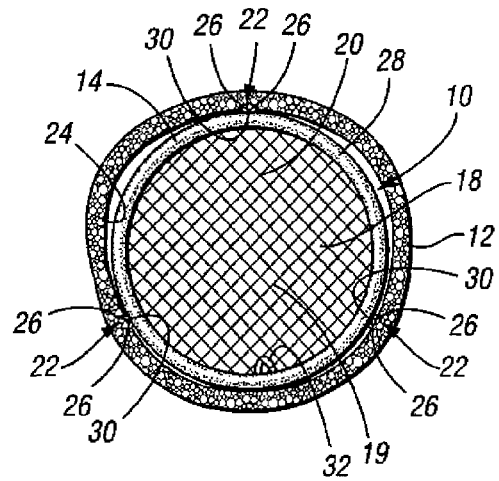
FIG. 2 is another environmental view of the occluding device in FIG. 1, taken along lines 2-2.

With reference to FIG. 2, the occluding device 10 is disposed within the body vessel 12 such that the outer edge 28 of the annular frame 14 substantially contacts the inside wall 24. That is, the entire outer edge 28 of the annular frame 14 preferably is in contact with the inside wall 24, so that fluid is unable to flow between the outer edge 28 and the inside wall 24.

The occluding device 10 further has an expanded state and a collapsed state. With reference to FIG. 2, the occluding device 10 is shown in the expanded state. In the expanded state, the occluding device 10 extends across the cross-section of the body vessel, thereby occluding fluid, blood clots, or any other object, material, or fluid traveling through the body vessel 12.

Figure 3:
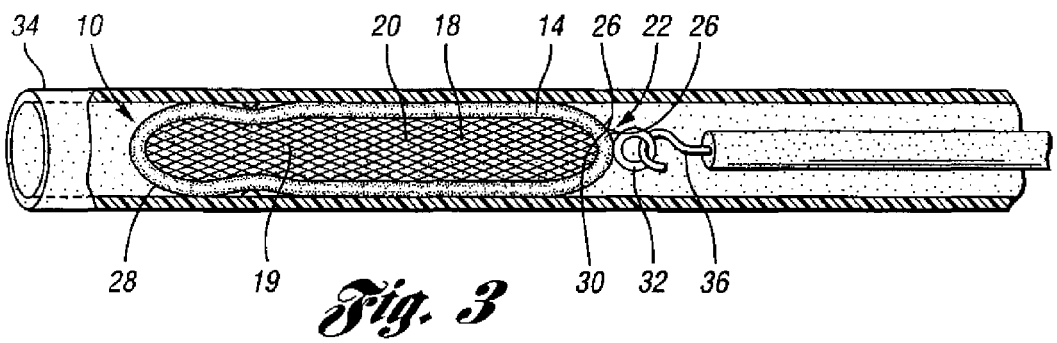
FIG. 3 is a side view of the occluding device of FIGS. 1-2 in a collapsed state.

With reference to FIG. 3, the occluding device 10 is shown in a collapsed state inside of a catheter 34. The catheter 34 is a thin tube used for inserting the device 10 into a body vessel 12 percutaneously, as is commonly known in the art. The catheter 34 is preferably made from a soft, flexible material, such as nylon, polytetrafluoroethylene (PTFE), a composite material, or any other suitable material.

When the occluding device 10 is in the collapsed state, the annular frame 14 is compressed into an elongate position, as shown in FIG. 3. In order to accommodate the elongate shape of the annular frame 14 in the compressed state, the membrane 20 is preferably stretchable, as in the case of a urethane membrane 20, or oversized, as in the case of a polyester fiber or SIS membrane 20.

The annular frame 14 is configured to self-expand into the expanded state and collapse into the collapsed state. When a force is exerted upon the outer edge 28 of the annular frame 14, the annular frame 14 may be compressed into its collapsed state as shown in FIG. 3 within the catheter 34. The occluding device 10 is inserted into the body vessel 12 in a collapsed state in order to minimize trauma to the vessel walls 24. When the device 10 is deployed from the catheter 34 into a body vessel 12, the device 10 self-expands to contact the vessel walls 24, moving from the collapsed state to the expanded state.

The annular frame 14 may be made of any suitable material that is capable of collapsing and expanding. For example, the annular frame 14 could be made of stainless steel, an alloy that includes nickel and titanium, such as Nitinol™, or an alloy that includes cobalt, chromium, nickel, molybdenum, and iron, such as Conichrome™.

With reference to FIGS. 1-3, the occluding device 10 has a coupling 32 attached to the outer edge 28 of the occluding device 10. The coupling 32 may be engaged by a hook 36 or other coupling means that is included as part of the catheter 34 or any other delivery device. In this way, the coupling 32 may be used to help position the occluding device 10 within the body vessel 12, or alternatively, reposition the occluding device 10 after the occluding device 10 is positioned within the body vessel 12.

Figure 4A:
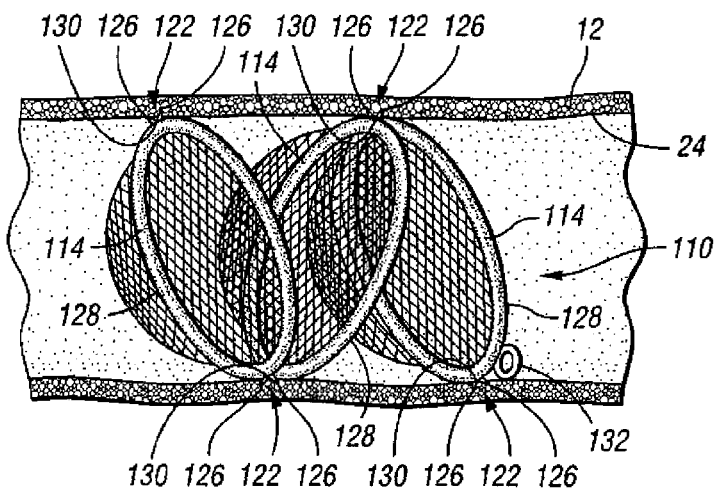
FIG. 4a is an environmental view of an occluding device in accordance with another embodiment of the present invention.

With reference to FIG. 4a, a second embodiment of the occluding device 110 is illustrated. The device 110 includes a plurality of annular frames 114, which are each substantially similar to the annular frame 14 of FIGS. 1-3. For example, the annular frame 14 comprises closure area 18, membrane 20, and anchoring components 22, and the annular frames 114 comprise closure areas 118, membranes 120, and anchoring components 122.

Each frame 114 is connected to one of the other frames 114, at their outer edges 128. In this embodiment, the occluding device 110 comprises three annular frames 114, each connected to at least one of the other frames 114. The frames 114 may be connected in any suitable way, without falling beyond the scope or spirit of the present invention. For example, the annular frames 114 could be integrally from one piece of frame material that is twisted to form the annular frames 114. Alternatively, or in addition, the annular frames 114 could be connected via welding or any other suitable connector or coupling. Preferably, the connections between the annular frames 114 are heat set to form the device 110 into a foldable, accordion-like shape, such that the device 110 is foldable for insertion into a catheter 134 and expandable to occlude within a body vessel 112.

Like the anchoring components 22 of the embodiment of FIGS. 1-3, the anchoring components 122 of the embodiment of FIGS. 4a-4b engage the tissue wall 24 of the body vessel 12 in order to help reduce migration of the device 110 within the body vessel 12. Each anchoring component 122 has a plurality of prongs 126 that extend from a point 130 that is located on the outer edges 128 of the frames 114. It is contemplated that a fewer number of anchoring components 122 is necessary on each annular frame 114 to engage the occluding device 110 of FIG. 4a-4b to the body vessel 112 than would be necessary on the annular frame 14 of the occluding device 10 of FIGS. 1-3, because twisting and migration of the device 110 is deterred by virtue of the device 110 having three annular frames 114, each having its own anchoring component(s) 122.

The occluding device 110 also has a coupling 132 through which the occluding device 110 may be positioned or repositioned inside the body vessel 12. The coupling 132 is attached to the outer edge 28 of one of the annular frames 114.

Like the embodiment of FIGS. 1-3, the occluding device 110 has an expanded state and a collapsed state. FIG. 4a shows the device in the expanded state, in which the device 110 is operable to occlude within the body vessel 12. With reference to FIG. 4b, the occluding device 110 is shown in the collapsed state within the catheter 134.

The catheter 134 is used to position the occluding device 110 within the body vessel 112. The catheter 134 has a hook 136 that engages the coupling 132 of the occluding device 110, in order to position or reposition the occluding device 110 within the body vessel 12. Upon deployment of the occluding device 110 from the catheter 134 into the body vessel 12, the occluding device 110 self-expands from the collapsed state into the expanded state, in order to occlude within the body vessel 12.

With reference to FIG. 5, a third embodiment of an occluding device 40 for occlusion within a body vessel 12 is illustrated. The occluding device 40 has an expandable body 42, for example, a stent. The expandable body 42 preferably has a plurality of elongate members 50 connected together to form the expandable body 42 into a cylindrical shape. The cylindrical-shaped expandable body 42 has an outer perimeter 44. The expandable body 42 could also have a coupling (not shown) for positioning or repositioning the device 40. Alternatively, the device 40 could be positioned or repositioned by engaging the elongate members 50.

An expandable balloon 52 is disposed about the expandable body 42, enclosing the expandable body 42 within the expandable balloon 52. As shown, the expandable balloon 52 has an open end 54. The open end 54 has an opening 56, which is configured to receive blood, or other bodily fluids or objects, into the expandable balloon 52 when the expandable body 42 expands, filling the balloon 52 to occlude the body vessel 12.

The expandable body 42 is configured to self-expand to the open state and collapse in the collapsed state. As the expandable body 42 self-expands inside of the expandable balloon 52, the expandable balloon 52 is also expanded. This allows the expandable balloon 52 to receive blood, or other fluid or objects, therein. When the expandable body 42 is in the open state, the outer perimeter 44 of the expandable body 42 engages the inside wall 24 of the body vessel 12. In this way, the occlusion device 40 is oversized with respect to the vessel wall 24. In the open state, the expandable body 42 is configured to be between about four millimeters and twenty millimeters, preferably, although it is contemplated that other dimensions could be used.

With reference to FIG. 6, the occlusion device 40 is shown in the collapsed state within a catheter 234. When the expandable body 42 is in the collapsed state, the elongate members 50 lie substantially parallel with respect to each other. With reference to FIG. 5, in the open state, the elongate members 50 form a grid pattern, or a "z" pattern, for example.

The catheter 238 has a deployment device 236 for positioning the occluding device 40 within the body vessel 12. After the occluding device 40 is deployed into the body vessel 12, via the catheter 238, the expandable body 42 self-expands from the collapsed state to the open state, thereby contacting the walls 24 of the body vessel 12. As the expandable body 42 expands into the open state, it pulls the expandable balloon 52 into the open state also. The expandable balloon 52 fills with blood, or other bodily fluids or objects, through its opening 56. When the expandable balloon 52 is full, the body vessel 12 will be occluded.

Figure 7:
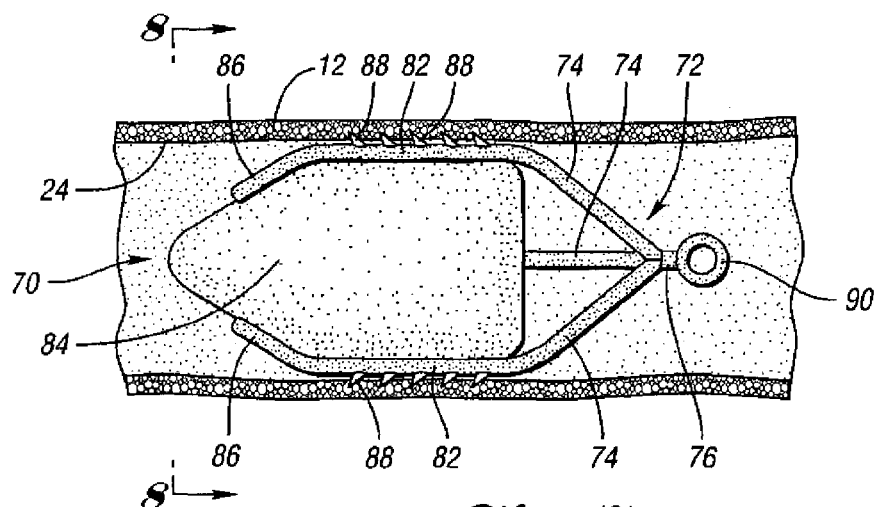
FIG. 7 is an environmental view of an occluding device in accordance with yet another embodiment of the present invention.
Figure 8:
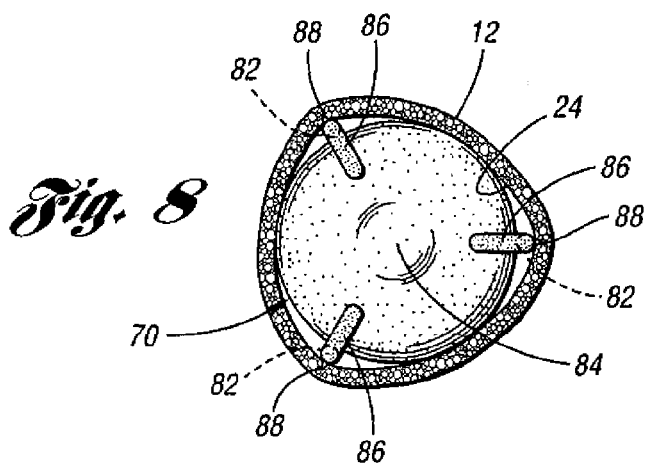
FIG. 8 is an end view of the occluding device of FIG. 7.

Referring now to FIGS. 7-8, another embodiment of an occluding device 70 is illustrated. The occluding device 70 is configured to be deployed into a body vessel 12, in order to occlude the body vessel 12.

In this embodiment, the occluding device 70 has a frame portion 72 that has struts 74 extending from a hub 76, defining a proximal portion. Each strut 74 extends from the hub 76, or proximal portion, to a second portion 82. The second portions 82 of the struts 74 are disposed about a compressible foam body 84. In this embodiment, the frame portion 72 has three struts 74. Preferably, the each strut 74 includes a third portion 86 that extends inwardly to help prevent the foam body 84 from migrating. The foam body 84 could alternatively be attached to the struts 74 by other means without falling beyond the scope or spirit of the present invention.

The second portions 82 of the struts 74 have anchoring components 88 to help reduce migration of the device 70 within the body vessel 12. The anchoring components 88 extend from the second portions 82 of the struts 74 and engage the inside walls 24 of the body vessel 12. The frame portion 72 has an expanded state and a collapsed state, which is described in further detail below.

The frame portion 72 may be made of any suitable material that is capable of collapsing and expanding. For example, the frame portion 72 could be made of stainless steel, an alloy that includes nickel and titanium, such as Nitinol™, or an alloy that includes cobalt, chromium, nickel, molybdenum, and iron, such as Conichrome™.

The foam body 84 is formed of compressible foam, such as urethane, polyurethane, polyvinyl alcohol, polyethylene, or any other suitable compressible material that is biocompatible. The compressible foam body 84 has a collapsed state and an expanded state. The frame portion 72 is configured to collapse in the collapsed state when the compressible foam body 84 collapses in the collapsed state. Likewise, the frame portion 72 is configured to expand in the expanded state when the compressible foam body 84 is expanded in the expanded state.

When in the expanded state, the compressible foam body 84 occludes the body vessel 12. The compressible foam body 84 may occlude by either blocking flow through the body vessel 12 or filling up with fluid, such as blood, or objects, such as clots, traveling through the body vessel 12. As shown, a coupling 90 is attached to the proximal portion or hub 76 of the frame portion 72. The coupling 90 may be used to position or reposition the occluding device 70 within the body vessel 12.

Figure 9:
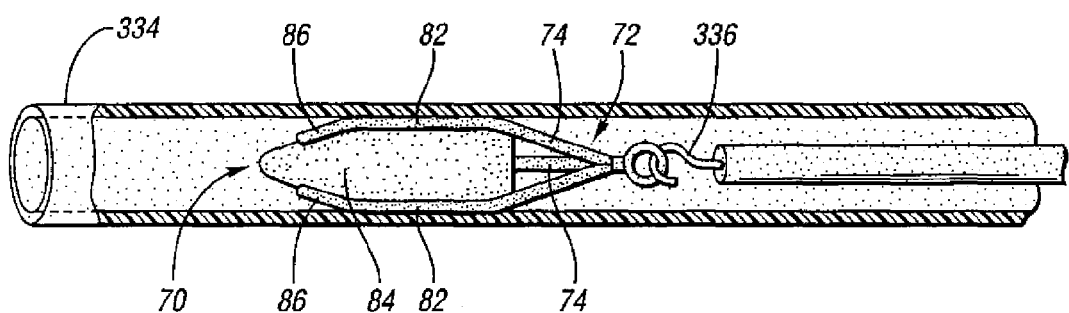
FIG. 9 is a side view of the occluding device of FIGS. 7-8 in a collapsed state.

With reference to FIGS. 7-8, when the occluding device 70 is disposed within the body vessel 12, the frame portion 72 and the compressible foam body 84 are in their expanded states, thereby engaging the vessel walls 24 and occluding the body vessel 12 by preventing fluid or objects from traveling past the occluding device 70 within body vessel 12. With reference to FIG. 9, the occluding device 70 is shown in its collapsed state within a catheter 334. The frame portion 72 is collapsed and the foam body 84 is compressed within the catheter 334, in order to insert the device 70 into a body vessel 12 with minimal damage to the walls 24 of the body vessel 12. The catheter 334 has a delivery portion 336, which engages the coupling 90 of the occluding device 70. The delivery portion 336 of the catheter 334 is used to position or reposition the occluding device 70 within the body vessel 12. When the occluding device 70 is deployed into the body vessel 12, the device 70 self-expands, contacting the walls 24 of the body vessel 12 and occluding the body vessel 12.

As a person skilled in the art will readily appreciate, the above description is meant as an illustration of implementation of the principles this invention. This description is not intended to limit the scope or application of this invention in that the invention is susceptible to modification, variation and change, without departing from the spirit of this invention, as defined in the following claims.

We claim:

1. An occluding device for occlusion of a body vessel, the device comprising:
    at least one frame having an expanded state and a collapsed state, the at least one frame having an outer edge defining a closure area therein, the at least one frame including at least one strut having a proximal end attached to a proximal portion, the at least one strut extending distally from the proximal end to a second portion, the second portion extending distally to a third portion, the third portion extending inwardly toward a longitudinal axis of the occluding device, the third portion being a linear segment having a proximal end that is attached to the second portion and a distal end that defines a distal end of the strut;
    an occluding portion having a proximal end and a distal end, the occluding portion being disposed within the closure area of the at least one frame, the occluding portion being disposed directly on the at least one frame, the proximal end of the occluding portion being disposed transverse to the longitudinal axis of the frame, the distal end of the occluding portion tapering such that a diameter of the distal end is smaller than a diameter of the proximal end, the third portion of the at least one strut being positioned to prevent the occluding portion from migrating and wherein the occluding portion extends distally of the distal end of the at least one strut;
    a plurality of anchoring components attached to the outer edge defining the closure area of the at least one frame on which the occluding portion is directly disposed such that the anchoring components are disposed only longitudinally and oppositely proximate the occluding portion, the anchoring components being configured to engage the occluding device with the body vessel for reduced migration of the device; and
    a coupling attached to the outer edge of the at least one frame for repositioning the occluding device.

2. The occluding device of claim 1, wherein the occluding portion comprises a membrane for occlusion of the body vessel.

3. The occluding device of claim 2, wherein the membrane comprises at least one of the following: small intestinal submucosa (SIS), synthetic polyester, and urethane.

4. The occluding device of claim 1, wherein the at least one frame is configured to self-expand into the expanded state; and
    the at least one frame is configured to collapse into the collapsed state upon exertion of a force to the outer edge of the at least one frame.

5. The occluding device of claim 1, wherein the plurality of anchoring component comprises a plurality of prongs extending from the outer edge of the at least one frame.

6. The occluding device of claim 1, wherein the at least one frame is comprised of at least one of the following: stainless steel, an alloy that includes nickel and titanium, and an alloy that includes cobalt, chromium, nickel, molybdenum, and iron.

7. The occluding device of claim 1, wherein the at least one strut is a plurality of struts, each strut of the plurality of struts being connected to at least one other strut of the plurality of struts.

8. The occluding device of claim 1 wherein the occluding portion comprises a compressible foam body.

9. The occluding device of claim 8, wherein the compressible foam body comprises a polyurethane foam.

10. An occluding device for occlusion within a body vessel, the device comprising:
    an occluding portion for occlusion within the body vessel, the occluding portion having a proximal end and a distal end;
    a frame comprising a plurality of struts having first ends attached together at a proximal portion, each strut extending distally from the first end to a second portion, the second portion extending distally to a third portion, the third portion extending inwardly toward a longitudinal axis of the frame to prevent the occluding portion from migrating, the third portion being a linear segment having a proximal end that is attached to the second portion and a distal end that defines a distal end of the strut, the second portions of each strut being disposed directly on the occluding portion, the proximal end of the occluding portion being disposed transverse to the longitudinal axis of the frame, the distal end of the occluding portion tapering such that a diameter of the distal end is smaller than a diameter of the proximal end, and the occluding portion extending distally of the distal end of the struts, the struts being configured to move between an expanded state for engaging the body vessel and a collapsed state for device retrieval or delivery, the second portions of the struts comprising at least one anchoring component such that the at least one anchoring component is disposed only longitudinally and oppositely proximate the occluding portion, the at least one anchoring component being configured to engage the body vessel when the struts are in the expanded state; and a positioning coupling extending from the proximal portion for delivering or repositioning the device.

11. The occluding device of claim 10, wherein the occluding portion is compressible and is comprised of polyurethane foam.

12. The occluding device of 10, wherein the plurality of struts is comprised of three struts.

* * * * *